United States Patent [19]

Cogburn

[11] Patent Number: 5,162,302

[45] Date of Patent: * Nov. 10, 1992

[54] ENDOCRINE MANIPULATION TO IMPROVE BODY COMPOSITION OF POULTRY

[75] Inventor: Larry A. Cogburn, New London, Pa.

[73] Assignee: University of Delaware, Newark, Del.

[*] Notice: The portion of the term of this patent subsequent to May 29, 2007 has been disclaimed.

[21] Appl. No.: 582,488

[22] Filed: Sep. 14, 1990

Related U.S. Application Data

[63] Continuation-in-part of Ser. No. 521,228, May 9, 1990, abandoned, which is a continuation-in-part of Ser. No. 169,737, Mar. 18, 1988, Pat. No. 4,129,600.

[51] Int. Cl.$^5$ .............. A61K 37/36; A61K 35/55; A61K 31/195
[52] U.S. Cl. ........................... 514/2; 514/21; 514/567; 424/568
[58] Field of Search ............... 514/2, 5, 21, 12, 567; 924/85.8, 568; 530/308

[56] References Cited

U.S. PATENT DOCUMENTS 4,929,600 5/1990 Cogburn .................. 514/2

Primary Examiner—Douglas W. Robinson
Assistant Examiner—Jean C. Witz

[57] ABSTRACT

The body composition of poultry is improved by a hormonal strategy that includes the steps of
(a) increasing plasma levels of thyroid hormone to at least about 150% (normal endogenous T$_3$ hormone level = 100%) during essentially the finishing phase (e.g., for chickens, 3 to 6 or 7 weeks-of-age) by administering (preferably orally) a metabolically-active thyroid hormone of the formula:

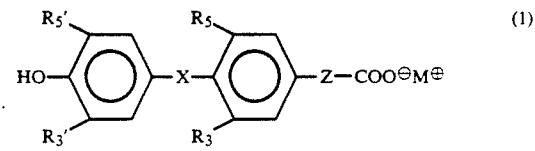

wherein X is O, S, or CH$_2$.
Z is C$_2$-C$_4$ alkylene or amino-substituted C$_2$-C$_4$ alkylene,
M$^+$ is a physiologically acceptable cation,
R$_3$ and R$_5$ are H or iodo, at least one of them being iodo,
R$_3'$ and R$_5'$ are iodo, or hydrogen or —A—COO—M$^+$, where A is C$_2$-C$_4$ alkylene and M$^+$ is a physiologically acceptable cation,
provided, that when R$_3'$, R$_5'$, R$_3$ and R$_5$ are all iodo, then Z—COO— is the residue of the anion of acetic or propionic acid, and
(b) increasing endogenous growth hormone by: providing exogenous growth hormone releasing factor (GRF), at least during the finishing phase (and preferably only during the finishing phase) and/or providing exogenous (preferably dietary) thyrotropin releasing hormone (TRH) during the finishing phase, or utilizing gene insertion techniques which result in high levels of endogenous GRF or growth hormone at least during the finishing phase.

11 Claims, No Drawings

ENDOCRINE MANIPULATION TO IMPROVE BODY COMPOSITION OF POULTRY

This application is a continuation-in-part of Ser. No. 521,228, filed May 9, 1990 abandonded, which is a continuation-in-part of Ser. No. 169,737, filed Mar. 18, 1988, now U.S. Pat. No. 4,929,600.

BACKGROUND OF THE INVENTION

This invention relates to a method for improving the carcass quality of poultry. An aspect of this invention relates to a manipulation of the hormone system of the poultry. Still another aspect of this invention relates to means and methods for altering blood levels of hormones in the bodies of poultry, which means and methods can be employed on a commercial scale.

DESCRIPTION OF THE PRIOR ART

A predominant cost in intensive production of poultry is the feed energy required for metabolism and growth. The metabolizable energy derived from feedstuffs is partitioned into energy for maintenance (i.e., thermoregulation and nutrient utilization) and the energy assimilated into animal product (meat or eggs). Advances in genetics, nutrition and management have provided producers with rapidly growing poultry produced for meat (broiler chickens, turkeys, and the like) that efficiently convert feed energy and nutrients into animal product. Unfortunately, excessive fat deposition is an undesirable consequence of the accelerated growth of poultry and high nutrient density of poultry rations. As the poultry reach market age, fat deposition—rather than protein accretion—becomes the principal component of weight gain. For example in broiler chickens, body fat represents from 7 to 20% of live market weight, with abdominal fat making up about 4% of total body weight. Since accumulation of excessive body fat is considered an economic loss to both the producer and consumer of poultry meat, recent research efforts have attempted to solve the problem of excessive fat deposition in the chicken's body. The inter-dependence of nutritional and genetic factors that determine accumulation of body fat precludes a uniform strategy for nutritional restriction of fat deposition. Furthermore, genetic selection against body fat would probably reduce live market weight as well as carcass quality.

Metabolically-active agents, such as hormones, appear to have the greatest potential for manipulating fat deposition and/or muscle development in animals raised for meat (see Kiernan et al., U.S. Pat. No. 4,407,819 issued Oct. 4, 1983). For example, injection of finishing pigs with purified porcine growth hormone (pGH) was found to increase growth rate by 10–14%, improve feed conversion by 7–19%, reduce carcass fat content by 18–25% and increase muscle mass by 24–36% (T. D. Etherton et al., *J. Anim. Sci.* 64:433–443, 1987). Similarly, daily administration of natural or recombinant-derived bovine GH (bGH) to dairy cows can increase milk yield by 23 to 41% (D. E. Bauman et al., *J. Dairy Sci.* 68: 1352–1362, 1985).

In contrast, however, these discoveries are not easily applied to poultry. Daily injection of broiler chickens with natural or recombinant-derived chicken GH (cGH) does not stimulate growth; in fact, cGH treatment usually results in increased accumulation of body fat (F. C. Leung et al., *Endocrinology* 118: 1961–1965, 1985; S. S. Liou et al., *Poultry Sci.* 64(Suppl. 1): 136, 1985; W. H. Burke et al., *Endocrinology*, 1987). Apparently, endocrine regulation of growth and metabolism in domestic fowl is distinctly different from that described for food mammals since exogenous cGH treatment alone does not promote growth or improve productive efficiency. The following summary of the relevant poultry science literature provides some insight into the comlexity of the research findings in this field.

Earlier work suggested that a synthetic iodinated protein, possessing thyroxine ($T_4$) activity, could be used as a feed additive to increase egg production or growth rate of domestic fowl (H. W. K. Jennings, British Patent 601,469, published in May of 1948). Iodinated casein (i.e., protomone) with 1% $T_4$ activity was originally developed as a possible growth promoter for poultry and livestock. However, the incorporation of protomone into the feed of meat-type chickens depressed growth rate, reduced feed efficiency, lowered carcass quality, and increased mortality rate when fed throughout the growth cycle (H. R. Wilson et al., *Poultry Sci.* 62: 811–818, 1983).

Triiodothyronine ($T_3$) and $T_4$ can be directly incorporated into the feed of broiler chickens for the purpose of elevating serum or plasma levels of thyroid hormones (J. D. May, *Poultry Sci.* 59:888–892, 1980; J. D. May, in *Aspects of Avian . . . Implications* (C. G. Scanes et al., eds.) Texas Tech Univ. Press 26: 185–189, 1982). This work has shown that treatment of normal broiler chickens with 0.25 to 1 parts per million (ppm) of dietary $T_3$ throughout the entire growth cycle reduced body weight gain and feed efficiency. In contrast, the same doses of dietary $T_4$ did not impair growth performance. The depressed growth rate and reduced feed efficiency of normal (euthyroid) broiler chickens fed 1 ppm $T_3$ throughout the growth cycle has led to the notion that dietary $T_3$ is detrimental to the growth and productive efficiency of poultry.

Attempts at using administration of exogenous GH to stimulate the growth of normal chickens have generally been unsuccessful. Daily intravenous injection of thyrotropin-releasing hormone (TRH) (1 or 10 $\mu g/kg$ of body weight/day) or GH-releasing factor (GRF, 10 $\mu g/kg$ of body weight/day) alone or in combination for 21 days failed to stimulate growth rate or improve feed efficiency of broiler chickens despite elevated plasma GH levels (F. C. Buonomo and C. A. Baile, *Dom. Anim. Endocrinol.* 4: 269–276, 1986). Most of the evidence for supporting the idea that exogenous GH is capable of promoting growth of broiler chickens is derived from studies on growth-compromised Leghorn (egg-type) chickens. In these studies, dwarf strains or hypophysectomized (i.e., pituitary gland surgically removed) Leghorns were given replacement doses of $T_3$, $T_4$ or GH (usually mammalian GH) alone or GH in combination with either $T_3$ or $T_4$ to determine the importance of these hormones in the normal growth process. The sex-linked dwarf Leghorn chicken has elevated plasma levels of both GH and $T_4$ whereas $T_3$ concentrations are greatly reduced. The depressed growth rate in dwarf strains of Leghorn chickens was restored to normal by supplementing their diets with either $T_3$ or $T_4$, or by the combination of $T_4$ with a daily injection of mammalian GH (J. A. Marsh et al., *Proc. Soc. Exp. Biol. Med.* 177: 82–91, 1984; and J. A. Marsh et al., *Proc. Soc. Exp. Biol. Med.* 175: 351–360, 1984). The importance of $T_3$ to the normal growth process was further demonstrated by the ability of exogenous $T_3$, rather than GH therapy, to correct the growth deficit of hypophysectomized Leghorn chickens (C. G. Scanes et al., *Growth* 50: 12-31, 1986). Although several studies have revealed distinct interactions between GH and the thyroid hormones in regulation of growth in chickens, this area clearly needs further research to develop a truely practical program of hormone manipulation which is useful on a commercial scale for normal, meat-type poultry.

Any hormonal treatment that restricts fat deposition while increasing carcass protein content could theoretically have a major impact on the cost and quality of poultry meat, and the formulation of poultry rations, but because poultry (particularly broiler chickens) are produced on such an enormous commercial scale, the treatment must satisfy a variety of practical criteria.

DEFINITIONS

Throughout this application, the following terms are used with the meanings indicated below.

"Finishing phase" or "finishing phase of the growth cycle" means the time period in the production of poultry after the major portion of the rapid growth of the avian species (e.g. broiler chickens and turkeys) has been completed. With modern broiler chicken production techniques, chickens grow to a high percentage of their live market weight in the first three to four weeks of life. Six or seven weeks of age is usually considered a market age for broiler chickens. Thus, the "finishing phase" for broiler chickens typically begins at about 3, 4 or (rarely) 5 weeks of age and lasts until slaughter, or a least until market age. In some embodiments of this invention, it may be desirable to permit the poultry to clear their bodies of any treatment for up to a week or so prior to slaughter. Thus, the "finishing phase" for broiler chickens can last as little as two weeks or as long as about five weeks, but in any case the rapid growth phase has been substantially completed before the "finishing phase" is underway. For turkeys, the growth cycle lasts longer (e.g. 15 to 25 weeks), hence the "finishing phase" begins after 6 weeks of age and may last longer than four or five weeks. It has now been found that circulating levels of endogenous $T_3$ (3,3',5-triiodo-L-thyronine) decrease during the "finishing phase" (as defined herein). Indeed, there is a very rapid rate of decline in plasma $T_3$ during this period. Accordingly, another way of defining the "finishing phase" of this invention is to test for the peak in endogenous plasma $T_3$, because the "finishing phase" of growth begins substantially immediately thereafter.

"Metabolically-active thyroid hormone" refers to the natural or synthetic iodinated D- or L- or DL-thyronine compounds or iodinated phenoxyphenol-substituted aliphatic carboxylic acids having more than 50% of the receptor binding capability of $T_3$ (3,3',5-triiodo-L-thyronine, alternatively 0-[4-hydroxy-3-iodophenyl]-3,5-diiodo-L-tyrosine) and preferably at least 30% of the in vivo activity of $T_3$. "Receptor binding" is defined herein in accordance with M. B. Bolger et al., *J. Biol. Chem.* 255: 10271-10278 (1980). Preferred metabolically-active thyroid hormones are compounds of the formula I:

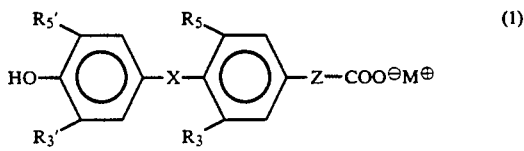

where

Z is $C_2$-$C_4$ alkylene or amino-substituted $C_2$-$C_4$ alkylene;

$M^+$ is a physiologically acceptable cation such as $H^+$;

$R_3$ and $R_5$ are hydrogen or iodine, at least one of them being iodine;

$R_3'$ and $R_5'$ are hydrogen or iodine or —A—COO $^-M^+$, where A is $C_2$-$C_4$ alkylene and $M^+$ is a physiologically acceptable cation; and X is a bridging radical such as —$CH_2$—, —S— or —O— (preferably —O—); provided, that if $R_3'$, $R_5'$, $R_3$ and $R_5$ are all iodine (I), then Z—COO$^-$ is a residue of the anion of acetic or propionic acid. The most active compounds of formula I are $T_3$ itself, "Triac" (Z=$CH_2$, M=H, $R_3$, $R_5$ and $R_3'$=I, $R_5'$=H) and "Tetrac" (similar to "Triac", except that $R_5'$=I). When Z is amino-substituted, the radical —Z—COO$^-$ can be the residue of D- or L- or DL-alanine.

BRIEF DESCRIPTION OF THE INVENTION

This invention is concerned with a novel, practical hormonal treatment for poultry grown for meat production, particularly broiler chickens, that reduces carcass fat and increases carcass protein content, without substantially detracting from normal growth. The treatment comprises (a) a carefully timed addition of about 0.01-3 parts per million of diluent (e.g. feed), i.e. 0.01-3 ppm, preferably 0.1 to 1 ppm of metabolically-active thyroid hormone, depending generally upon the activity of the thyroid hormone, the degree of decrease in fat deposition desired, the degree of deviation from normal growth which can be tolerated, etc. (b) a method for increasing endogenous growth hormone (GH), e.g. with a dosage of exogenous growth hormone releasing factor (GRF), which dosage may be timed to coincide with the first aspect of the treatment (and preferably is so timed). Other methods for increasing endogenous GH levels involve the use of exogenous TRH or the introduction of a suitable fusion gene into the somatic tissue or the germ line of the poultry. The administration of the GRF requires somewhat lower levels of administration of metabolically active thyroid hormone as compared to the levels of thyroid hormone that would be used in the absence of GRF administration. Thyroid hormones, particularly $T_3$, inhibit synthesis and secretion of GH from the pituitary gland.

The preferred metabolically active thyroid hormone is triiodothyronine ($T_3$, 3,3',5-triiodo-L-thyronine or 0-[4-hydroxy-3-iodophenyl]-3,5-diiodo-L-tyrosine), and the preferred route of administration is oral; accordingly, it is particularly preferred to add the metabolically active thyroid hormone to the feed of broiler chickens. It is important that the metabolically-active thyroid hormone be given during the finishing phase (usually 3 to 7 weeks-of-age). The consumption of feed containing the preferred amount of $T_3$ provides broiler chickens with a 50 to 150% elevation of plasma $T_3$ levels when compared to controls. The efficacy of this invention is enhanced when, in addition to providing poultry with dietary $T_3$ during the finishing phase, GH (somatotropin) or glucagon levels in the bloodstream are also increased, or glucagon levels are increased relative to insulin levels, also during the finishing phase and preferably by 2- to 10-fold. In one embodiment of this invention, poultry are provided with dietary $T_3$ during the finishing phase and circulating levels of glucagon relative to insulin are increased, i.e., the insulin-to-glucagon (I/G) molar ratio is decreased. Since the timing of applying the dietary $T_3$ treatment alone or dietary $T_3$ in combination with GRF to broiler chickens is of very great significance and should be substantially limited to the finishing phase, the rapid growth phase of the chickens should be substantially concluded when the treatment begins, and treatment will typically last for two to five weeks. A GRF injection or implantation can take place prior to the finishing phase, alone or in combination with injection or implantation of thyroid hormone, if slow or delayed release, techniques are employed, so that the GRF is actually provided during the finishing phase. When the timing of dietary metabolically-active thyroid hormone is controlled in accordance with this invention, and when the amount of this hormone is selected in accordance with criteria described subsequently, no statistically significant impairment of growth is observed. This result is surprising in view of previous experience with $T_3$ given throughout the growth period of poultry.

This invention is not bound by any theory. Available data suggest that metabolically active thyroid hormone manipulation within the scope of this invention can have a useful effect upon several variables such as I/G molar ratio of the avian pancreatic hormonal system, accretion and/or degration of protein. It is presently theorized that a decrease in the I/G molar ratio of poultry during the finishing phase mobilizes body fat stores, and, if a carefully controlled amount of metabolically-active thyroid hormone is used, body fat content is reduced. In the case of $T_3$ specifically, the optimum range of content in feed appears to be about 0.1 to 1 ppm. The GRF provides GH enhancement which cooperates with the $T_3$ or other metabolically-active thyroid hormone to provide much greater reductions in body fat than would be achieved with $T_3$ above.

DETAILED DESCRIPTION OF THE INVENTION

The above mentioned metabolically-active hormones are naturally synthesized within the body of domestic fowl and are known to be important regulators of various metabolic activities (i.e., energy, carbohydrate, lipid and protein metabolism) that contribute to normal growth and development. It is relevant to note that there are three major groups of metabolically-active hormones: (1) pituitary hormones [GH, prolactin and thyroid-stimulating hormone (TSH)] and their hypothalamic releasing factors [GH-releasing factor (GRF), GH-release inhibiting factor or somatostatin (SRIF), and thyrotropin-releasing hormone (TRH)], (2) the thyroid hormones ($T_3$ and $T_4$), and (3) the pancreatic hormones (insulin, glucagon and somatostatin). The natural metabolically-active hormones, synthetic analogues and their pharmacologically-acceptable salts are to be considered within the scope of this invention. Amino acid components or residues and carbohydrate components of synthetic metabolically-active substances are generally provided in the most active isomeric forms (e.g. L-amino acids, D-carbohydrates, etc.), except that racemates (DL-compounds), diastereomers, etc. can be used when sufficient normal physiological activity is still obtained, e.g. 50% of the active (D- or L-) form. Analogs of $T_3$ containing a D-amino acid residue can be active, apparently because of the importance of the location of other substituents on the molecules. This invention is concerned with means of enhancing circulating blood levels of certain metabolically-active hormones including the thyroid hormones (particularly $T_3$). In this invention GRF or GRF and pancreatic hormone levels are also manipulated.

The secretion of trophic hormones from the pituitary gland is regulated by releasing or inhibiting factors secreted by the hypothalamus. Of relevance to this invention, are the releasing factors that regulate secretion of TSH and pituitary GH (somatotropin). Thyrotropin-releasing hormone (TRH) stimulates the release of both TSH and GH from the avian pituitary gland into the bloodstream. Under the stimulating effect of TSH, the thyroid gland predominately synthesizes and secretes $T_4$ (3,5,3', 5'-tetraiodothyronine) into the blood. The enzymatic activity of thyroxine-5'-monodeiodinase in peripheral tissue (particularly the liver and kidney) is responsible for converting $T_4$ into metabolically-active $T_3$. The positive or stimulative pathway is represented by: TRH→pituitary→TSH→thyroid→$T_4$→5'-monodeiodinase activity→$T_3$. It is generally accepted that $T_4$ is a prohormone without significant metabolic activity and that any benefit derived from treatment of animals with exogenous $T_4$ is derived from its conversion, via 5'-monodeiodinase activity, into metabolically-active $T_3$. Thus, the attempts at stimulating the growth or productive efficiency of domestic animals (poultry and livestock) with iodinated protein (i.e., protomone) that is based on thyroxine activity (see Jennings, British Patent 601,469 dated May 6, 1948) are of questionable efficacy since thyroxine ($T_4$) is essentially inactive in provoking metabolic and hormonal responses. In birds, circulating $T_3$ levels play an important role in regulating metabolic heat production and secretion of pituitary and pancreatic hormones. It is apparent from the working Examples which follow that $T_3$ also regulates the secretion of insulin and glucagon from the avian pancreas. All embodiments of this invention have in common the administration (preferably dietary) of metabolically-active thyroid hormone (preferably $T_3$ or a compound of Formula I, above, which has biological activity comparable to $T_3$) to poultry during the finishing phase, but not significantly prior to the finishing phase. During the finishing phase, the GH (somatotropin) naturally secreted by the poultry has already done much of its work, and there is no significant losses in body weight or protein content during this phase. There is, on the other hand, a more rapid utilization of body fat as a result of the orally-administered Formula I compound.

This invention enhances or even synergizes effectiveness of the metabolically-active thyroid hormone treatment by increasing blood levels of GH or by decreasing the insulin/glucagon (I/G) molar ratio. The timing of this enhancement effect need not be exactly coextensive with the metabolically-active thyroid hormone treatment, but it is believed to be most useful to decrease the I/G molar ratio only during the finishing phase. GRF treatment is also useful substantially only during the finishing phase, but GRF treatment prior to the finishing phase appears to have little or no adverse impact upon weight gain, protein accretion, the limitation of fat accretion, etc. In the context of this invention, the timing of the "providing" of GRF should be understood to mean the time that the GRF becomes available to the bird's growth-regulation system. Accordingly, if a delayed-release technique is used, the GRF may be injected, in delayed-release form, just after the bird is hatched, but the GRF will not be "provided" until the bird is more than two weeks old. (In the case of TRH or its analogs, discussed subsequently, dietary administration is possible, hence the administration of the TRH or TRH analog can be precisely timed and can be limited to the finishing phase of the life cycle of the poultry, without resort to any delayed release technology.)

The enhancing of blood levels of endogenous GH is achieved by administration of one of the hypothalamic releasing factors that provoke endogenous GH secretion from the pituitary gland, i.e. GRF or TRH. Human GRF is a 44 amino acid polypeptide hormone with a molecular weight of 5040 (R. Guillemin et al., *Science* 218: 585–587, 1982) that stimulates endogenous GH secretion from the pituitary gland (see Chang et al. U.S. Pat. No. 4,562,175 issued Dec. 31, 1985). Subsequent to the isolation and characterization of human GRF, the amino sequence has been determined for rat (J. Spiess et al., *Nature* 303: 532–535, 1983), porcine (P. Bohlen et al., *Biochem. Biophys. Res. Comm.* 116: 726–734, 1983), bovine (F. Esch et al., *Biochem. Biophys. Res. Comm.* 117: 772–779, 1983), caprine, and ovine (P. Brazeau et al., *Biochem. Biophys. Res. Comm.* 125: 606–614, 1984) forms of GRF. Apparently only the first 29 amino acids (i.e., GRF 1–29) are required for GH-releasing activity; therefore, numerous synthetic analogues have been developed that range from GRF 1–29 to GRF 1–44. Although an avian GRF has not yet been isolated and characterized, a number of these analogues possess the ability to provoke endogenous GH secretion from the chicken's pituitary (C. G. Scanes et al., *Life Sci.* 34: 1127–1134, 1984; and C. G. Scanes et al., *J. Endocrinol.* 108: 413–416, 1986). Within the context of this invention are all the pharmaceutical acceptable salts of the natural, recombinant-derived and synthetic analogues of GRF which stimulate GH secretion from the avian pituitary gland. The route of administration of GRF (including synthetic GRF containing only 29 amino acids) can be oral, parenteral or by prolonged-release implant or other slow-release or delayed-release techniques or by gene insertion (described subsequently). It is an advantageous feature of this invention that, instead of administering cGH, a 191 amino acid protein hormone, exogenous GRF (a polypeptide hormone ranging from 1–29 to 1–44 amino acids) can be used to increase endogenous cGH secretion.

Another method of enhancing endogenous GH secretion in domestic fowl is the use of TRH—a tripeptide releasing factor (pyro-L-Glu-L-His-L-Pro-NH₂) secreted by the hypothalamus that provokes the secretion of GH and TSH from the avian pituitary. Daily intravenous injection of 1 to 10 μg TRH/day from 4 to 6 or 8 weeks-of-age is capable of increasing the growth rate of broiler chickens (Leung et al., U.S. Pat. No. 4,493,828 issued Jan. 15, 1985). An obvious advantage of using TRH treatment as a means of enhancing GH secretion in broiler chickens is that this hypothalamic releasing factor is orally-active and can be incorporated into the feed or drinking water of poultry (Snarey et al., U.S. Pat. No. 4,562,197, issued Dec. 31, 1985). The disadvantage of this approach of stimulating GH secretion is that TRH is a non-selective releasing factor which provokes the release of at least two pituitary hormones (i.e., TSH and GH). Recent advances in hormone research have, however, resulted in the development of TRH analogs which stimulate essentially only the somatotropic cells of the pituitary gland or essentially only the thyrotropic cells of the pituitary gland. The TRH analogs which selectively stimulate the somatotropic cells do not provoke any substantial release of TSH. Within the scope of this invention is the use of orally-active TRH or somatotropic cell-specific analogs of TRH applied in either the feed or drinking water of poultry to increase GH secretion during the finishing phase of the growth cycle. It can be advantageous to utilize TRH or a TRH analog in combination with GRF, hence the use of such combinations is also within the scope of this invention.

Still another method of enhancing circulating blood levels of GH is the introduction of a fusion gene into somatic tissue or the germ line of poultry which leads to expression of copious amounts of GH in circulation or greater expression of GRF (i.e., production of "transgenic chickens"). The microinjection of fertilized mouse ova with a hybrid fusion gene carrying the metallothionein (MT) promoter region and the structural gene which codes for either rat or human GH (i.e., a MT-GH fusion gene) results in a dramatic increase in body growth due to hypersecretion of GH (R. D. Palmiter et al., *Nature* 300: 611–615, 1982; and R. D. Palmiter et al., *Science* 222: 809–814, 1983). These transgenic mice typically show increases of 100- to 800-fold

| Human Growth Hormone-Releasing Factor | | | | | | | | |
|---|---|---|---|---|---|---|---|---|
| 1 Y A D A I F T N S Y R K V L G Q L S A R K L L Q D I M S R Q | | | | | | | | |
| 31 Q G E S N Q E R G A R A R L-NH₂ | | | | | | | | |
| Composition | | | | | | | | |
| 5 | ALA | A | 5 | GLN | Q | 5 | LEU | L | 4 | SER | S |
| 6 | ARG | R | 2 | GLU | E | 2 | LYS | K | 1 | THR | T |
| 2 | ASN | N | 3 | GLY | G | 1 | MET | M | 2 | TYR | Y |
| 2 | ASP | D | 2 | ILE | I | 1 | PHE | F | 1 | VAL | V |

Mol. wt. = 5040
Number of residues = 44
R. Guillemin et al., Science 218:585–587, 1982

As noted above, it is not essential in this invention to use a 44 amino acid GRF. Synthetic GRF analogs having only 29 amino acids are available, including GRF analogs with at least one D-alanine residue (e.g. two such residues) inserted in the polypeptide chain, so that the GRF analog will be more resistant to enzymatic breakdown. These D-alanine containing GRF analogs have much longer biological half-lives than 29- or 44-unit polypeptides containing only L-amino acid residues.

in serum GH levels and grow to twice the normal body size. Thus, gene insertion technology has tremendous potential for selective growth stimulation and/or improvements in productive efficiency of domestic animals. In fact, transgenic rabbits, pigs and sheep have been produced by microinjection of the MT-GH fusion gene (R. E. Hammer et al., *Nature* 315: 680–683, 1985). Furthermore, the introduction of a MT-GRF fusion gene into mice also results in increased body growth in the MT-GRF transgenic mice due to hypesecretion of GRF and, consequently, increased secretion of pituitary GH (R. E. Hammer et al., *Nature* 315: 413–416, 1985). However, the nature of ovulation and fertilization of the ovum in birds does not allow microinjection of hybrid fusion genes into the fertilized ovum. Souza et al. (*J. Exp. Zool.* 232: 465–473, 1984) have developed a recombinant retrovirus (i.e., a Rous sarcoma virus) vector that contains the entire coding region for cGH (designated SRA-cGH9). Infection of 9-day-old chicken embryos with the SRA-cGH9 retrovirus vector resulted in 3- to 10-fold increases in serum GH levels in the hatched chickens.

Although this invention is not bound by any theory, an aspect of this invention is believed to involve the molar ratio of insulin-to-glucagon (I/G) secreted into blood by the endocrine pancreas. Endocrine regulation of metabolism in birds is distinctly different from that of mammals because glucagon is the pancreatic hormone that regulates blood glucose levels in birds, and because fat synthesis (i.e., lipogenesis) takes place in the liver of birds (R. L. Hazelwood, in *Avian Physiology*, P. D. Sturkie, ed., Springer-Verlag, pp. 303–325, 1986). In birds, glucagon exerts a strong catabolic action by mobilizing free fatty acids from adipose tissue (i.e., a lipolytic action) whereas insulin promotes anabolic activities (i.e., glucose uptake, the formation and storage of glycogen, etc.). Thus, the I/G molar ratio serves as the prime determinant of metabolic homeostasis in birds (R. L. Hazelwood, *J. Exp. Zool.* 232:647–652, 1984). A high els and increased accumulation of body fat (K. L. Raheja et al., *Horm. Metab. Res.* 12: 51–55, 1980; and Example 1 below). Furthermore, there is sufficient experimental evidence to support the idea that providing poultry with dietary $T_3$ and exogenous glucagon (by injection, implant or orally-active analogues of glucagon) would achieve the same benefits and improvements in body composition as the combination of dietary $T_3$ with any other treatment that simultaneously enhances circulating GH concentrations. This invention contemplates the use of exogenous glucagon treatment in combination with dietary $T_3$ as the most simple version of an endocrine manipulation designed to reduce body fat content of poultry.

Glucagon is a highly conserved polypeptide hormone which has an identical amino acid sequence among mammals. Chicken and turkey glucagon differ from mammalian glucagon by the single substitution of serine (SER) for asparagine (ASN) at position 28 (R. L. Hazelwood, *J. Exp. Zool.* 232: 647–652, 1986). The amino acid sequence of duck glucagon differs from other birds (chicken and turkey) due to the single substitution of threonine (THR) for serine (SER) at position 16. Because of these structural similarities, the commercial preparations of glucagon from the pancreases of slaughtered cattle and swine have the same biological and metabolic activity as endogenous glucagon when injected into chickens.

| Chicken Glucagon | | | | | | | | | |
|---|---|---|---|---|---|---|---|---|---|
| 1 H S Q G T F T S D Y S K Y L D S R R A Q D F V Q W L M S T | | | | | | | | | |
|                    10                  20             30 | | | | | | | | | |
| Composition | | | | | | | | | |
| 1 ALA | A | 3 GLN | Q | 2 LEU | L | 2 PHE | F | 1 TRP | W |
| 2 ARG | R | 1 GLY | G | 1 LYS | K | 5 SER | S | 2 TYR | Y |
| 3 ASP | D | 1 HIS | H | 1 MET | M | 3 THR | T | 1 VAL | V |

Mol. wt. = 3,485
Number of residues = 29
R. L. Hazelwood, "Carbohydrate Metabolism", in Avian Physiology, P. D. Sturkie ed., Academic Press, pp. 303–325, 1986.

I/G molar ratio indicates that the bird is in an anabolic mode (i.e., nutrient storage) while a low I/G molar ratio reflects the catabolic state (i.e., nutrient utilization). The avian pancreas also produces an exceptionally large quantity of SRIF which is thought to be an important regulator of the I/G molar ratio. Of particular interest is the fact that pancreatic SRIF is a potent inhibitor of glucagon secretion in chickens; therefore, it appears that immunoneutralization of SRIF, designed to promote pituitary GH secretion, can also enhance glucagon secretion from the pancreas.

Experimentation carried out in support of this invention indicates that administration of exogenous ncGH by injection and $T_3$ dietary treatment during the finishing phase of the chicken's growth cycle ultimately alters the I/G molar ratio. The metabolic events that lead to the dramatic depletion of body fat content are brought about by a reduction in the I/G molar ratio (i.e., reduced insulin and elevated glucagon levels in blood) and an increase in circulating $T_3$ levels. This concept is supported by the observation that dietary $T_3$ treatment alone depresses insulin secretion while glucagon secretion is increased (i.e., a reduced I/G molar ratio) and consequently decreases fat deposition in chickens. Treatment of chickens with propylthiouracil, a goitrogen that inhibits 5'-monodeiodinase activity and therefore the conversion of $T_4$ into $T_3$, induces a hypothyroid state that results in elevated plasma insulin lev- Because of the ease and convenience of administration of orally-active hormones or hormone stimulants or suppressants through poultry feed, one of the embodiments of this invention involves a finishing feed which contains physiologically effective amounts of metabolically-active thyroid hormone (preferably $T_3$), alone or in combination with other orally-active compounds which stimulate or suppress hormone secretion. Finishing feeds typically contain a major amount (e.g. 60–90% by weight) of ground-up grain (corn, soybeans, etc.), a modest amount of fat (e.g. <10%), salts, vitamin and mineral premixes, amino acids, etc. The protein content is typically above 15% (e.g. 17–25% by weight), and some fiber content should be present.

Regardless of which embodiment of this invention is used, no radical changes in feed compositions or daily ration weights are necessary; indeed, conventional finishing feed formulas and amounts (except for the addition of dietary thyroid hormone and, if desired, orally active GH— or glucagon-increasing agents) are fully operative in this invention. The health of the birds does not appear to be adversely affected, and essential body functions (e.g. thermoregulation) do not appear to be adversely affected. However, economically advantageous changes in energy and/or protein content of finishing feeds are made possible by this invention.

Referring now to broiler chickens as a benchmark for the beneficial effects of this invention, it must be noted that these chickens grow from a weight of 30 to 50 grams at hatching to about 1.5-3 or even as much as 5 kilograms of body weight at market age. Of this market weight, 15-20 wt.-% is protein, 2-3 wt.-% is inorganic (showing up as ash in proximate analysis of body composition), and more than 10 wt.-% (e.g. 10-20 wt.-%) is fat, which means that the protein: fat ratio (by weight) is likely to be at or below 1.5:1 and certainly well below 2:1. In broiler chickens treated according to this invention, however, protein: fat ratios above 1.6:1 and even above 2:1 have been obtained, due to decreases in carcass fat content exceeding 15 wt.-%. A comparable increase in the protein:fat ratio was not obtained with $T_4+GH$ treatment (although some improvement was found); $T_4$ treatment alone had almost no effect upon this ratio: and various other treatments actually seemed to decrease the protein:fat ratio at the doses tested (e.g. GH alone, TRH alone, TRH+GH, and propylthiouracil alone).

DOSAGE OF METABOLICALLY ACTIVE THYROID HORMONE

As noted previously, the preferred dosage of exogenous metabolically active thyroid hormone (e.g. the concentration of $T_3$ in finishing feed) is a variable which depends upon a variety of objectives and parameters such as effectiveness of the thyroid hormone, the desired degree of control over fat accretion, the desired degree of protein accretion, the degree of deviation from normal growth which can be tolerated, and the like. The receptor binding capacity thyroid hormones useful in this invention can vary from 50% ($T_3=100\%$) to well in excess of 100%. Some synthetic $T_3$ analogs are more active than $T_3$ itself by a factor of three or four. Accordingly, any of these highly active analogs, used as feed additives, can be present to the extent of only about 0.01 parts per million of the feed and still have a measurable effect upon fat accretion. At the other extreme, a $T_3$ analog or a $T_3$ racemate with less than the activity of $T_3$ (e.g. 50% of the receptor binding capacity) could be present at levels up to 3 ppm of feed without causing intolerable or unacceptable effects upon weight gain or body composition.

Using $T_3$ itself as a standard, the preferred content or dose finishing feed is preferably much less than 3 ppm, because some deviation from normal weight gain is observed even at 1 ppm dose. At 0.1 ppm, on the other hand, no significant adverse effect upon weight gain can be detected, yet the protein content of the carcass is improved relative to fat content. The increased protein accretion appears to be due to decrease in fat deposition combined with a good protein Fractional Accretion Rate (FAR). Protein FAR is determined by measuring the Fractional Synthesis Rate (FSR) and Fractional Degradation Rate (FDR) and finding the difference between these rates, i.e.

$$FAR=FSR-FDR$$

At very low dosages of exogenous $T_3$ (e.g. 0.1 to 0.5 ppm, based on the weight of the finishing feed), protein FAR is close to or within normal limits or enhanced (despite the tendency of $T_3$ to depress GH levels), and fat deposition is suppressed. A dosage of 0.25 parts $T_3$ per million parts of feed presently appears to be very close to optimum, because the protein accretion rate was higher, the body fat of the birds is decreased by as much as 20 to 25%, and virtually no statistically significant adverse effect on growth rate is observed.

The consumption of finishing feed containing $T_3$ or a metabolically active $T_3$ analog appears to elevate plasma thyroid hormone levels in a dose-dependent manner. In the case of $T_3$, a typical dose-response relationship is as follows.

| Amount of $T_3$ in feed | Plasma $T_3$ level (control group = 100% of normal) |
|---|---|
| 0 ppm | 100% (1.3 ± 0.1 ng/ml) |
| 0.25 ppm | ~208% (2.7 ± 0.2 ng/ml) |
| 1 ppm | ~346% (4.5 ± 0.8 ng/ml) |
| 4 ppm | ~125% (16.3 ± 2.6 ng/ml) |

The optimum increase in plasma $T_3$ level appears to be 50-150%, i.e. 150 to 250% of the normal level. Accordingly, when a $T_3$ analog is used, the dosage is preferably adjusted to provide a plasma thyroid hormone bioactivity level corresponding to 150-250% of the normal level. (It should be borne in mind that the normal exogenous plasma $T_3$ levels are in a rapid state of decline during the "finishing phase".) When the level of plasma thyroid hormone bioactivity is 360-1200%, body weight gain can be depressed by as much as 57%, and feed consumption can be depressed by as much as 35%; moreover, accretion of certain muscle protein (particularly breast muscle) is decreased, because the rate of protein breakdown greatly exceeds the rate of protein synthesis.

The fractional synthesis rate (FSR) of the pectoralis major (breast) muscle was increased ($p<0.05$) by 56% in chickens fed 4 ppm of $T_3$ whereas this dose of $T_3$ increased the fractional degradation rate of breast muscle by 116%. A wide range of dietary $T_3$ doses (0.25 to 4 ppm of feed) increased ($p<0.05$) the rate of protein synthesis in the leg muscle of broiler chickens by at least about 49%. The lower doses of $T_3$ (0.25 to 1 ppm) had only a slight effect upon protein synthesis rate in breast muscle, but these lower doses, particularly the 0.25 ppm dose, were much more desirable in terms of the Fractional Degradation Rate (FDR) of protein in breast muscle. Accordingly, Fractional Accretion Rate (FAR) in the pectoralis major (breast) muscle was affected negatively by $T_3$ doses in the 1 to 4 ppm range, whereas the effect was positive at the 0.25 ppm level. The positive effect upon FAR in leg muscle was better for the birds fed 0.25 ppm $T_3$ than the birds fed 1.0 or 4.0 ppm $T_3$. In fact the 0.25 ppm dose of $T_3$ increased the FAR of pectoralis major (breast muscle) by 88% and the FAR of leg muscle by 45% when compared to the control group. Therefore the lowest dose of $T_3$ (0.25 ppm) appears to be near optimal since this dose reduces abdominal fat weight by 22% while protein accretion in breast and leg muscle was increased by 45-88%.

Dietary $T_3$ administered according to this invention has now been found to decrease plasma GH levels and to alter plasma levels of insulin and glucagon. The lower GH levels observed in chickens fed 0.25 ppm $T_3$ do not appear to have a statistically significant effect upon final body weight, however.

Surprisingly, these data suggest that metabolically active thyroid hormone can be caused to be more important than GH levels in stimulating certain kinds of growth in chickens and maintaining a favorable protein turnover rate, particularly during the last part of the growth period. Significant loss of growth rate is observed when $T_3$ administration exceeds the guidelines set by this invention and can even be disastrous from the standpoint of marketability of the carcass or keeping the growthperiod sufficiently short for economic practicality. Significant loss of growth rate is also observed when the period of administering dietary $T_3$ extends too far back into the rapid growth part of the growth period.

When the guidelines discovered for this invention are observed, significant improvement in the body compositions of market-ready broiler chickens can be obtained through the administration of dietary metabolically-active thyroid hormone. Because of the convenience and economic attractiveness of this very simple hormone manipulation, the use of readily available metabolically active thyroid hormones (such as $T_3$) in the diet of broiler chickens (after the rapid growth phase is completed) is a preferred way to administer these hormones. Other preferred techniques of administration involve delayed release technology, particularly when thyroid hormone is coadministered with GRF.

Although this invention is not bound by any theory, one could theoretically describe this invention as a method for counteracting the rapid decline in endogenous $T_3$ levels during the "finishing phase" of the growth period of poultry, and by counteracting this decline with carefully timed and carefully measured doses of $T_3$, fat accretion is inhibited while favorable protein turnover is maintained or even improved. The high level of protein FAR is surprising in view of the tendency of $T_3$ to suppress GH levels (probably by inhibiting synthesis and secretion of GH by the pituitary gland).

A possible theoretical reason for the synergistic effect of $T_3$+endogenous GH or $T_3$+GRF administration in endogenous GH can partially or even fully counteract the lowering of the endogenous GH levels caused by the increased plasma thyroid hormone.

EXAMPLES

In the Examples which follow, the principle and practice of this invention are illustrated. To provide maximum scientific control over the results, GRF was administered by multiple daily intramuscular or intravenous injections even though this technique of administration would not normally be used in commercial practice. The following abbreviations are used in these Examples:

CF=control feed
$T_3$=3,3',5-triiodo-L-thyronine
$T_4$=thyoxine
GH=growth hormone (e.g. ncGH, natural chicken GH)
GRF=growth hormone releasing factor
BW=body weight
ADG=average daily weight gain
ADFC=average daily feed consumption
BI=bicarbonate buffer injection
N=number of test chickens
SEM=standard error of the mean

EXAMPLE 1

Effect of Three Daily Intramuscular Injections of Growth Hormone Releasing Factor and Dietary Triiodothyronine on Growth, Feed Efficiency, and Body Composition of Broiler Chickens The purpose of this Example was to determine if multiple daily intramuscular injections of growth hormone-releasing factor (GRF) and dietary triiodothyronine ($T_3$) could be used to increase lean body mass of broiler chickens fed a high protein ration.

MATERIALS AND METHODS

Bird management. One day-old broiler cockerels (Ross x Arbor acre) were obtained from a commercial hatchery (Perdue Hatchery, Salisburg, MD). Five birds were randomly assigned to each of 24 pens during the first three weeks. Birds were housed in a Petersime battery-brooder and maintained in a environmentally controlled room on a 20L:4D light/dark cycle. The temperature was held at 33° C. for the first week and reduced 3° C. at weekly intervals. During this period, the chicks were provided with commercial starter ration (3100 kcal ME/kg and 22% crude protein) and water ad libitum.

At 3 weeks-of-age, four birds per pen were moved to wire cages. From 3 to 4 weeks of age, birds were fed a commercial broiler grower/finisher ration containing 19% crude protein and 3200 kcal metabolizable energy/kg. At 4 weeks of age, birds were fed a special high-protein ration that contained 25% crude protein and 3250 kcal ME/kg feed (See Table 1). From 5 to 7 weeks of age, birds were fed this ration containing either dextrose premix [i.e., control feed, (CF)] or 0.25 parts per million (ppm) of triiodothyroinine ($T_3$). During the experimental period (5 to 7 weeks of age), individual body weights and feed consumption were determined at weekly intervals for calculation of average daily gain (ADG), average daily feed consumption (ADFC) and gain-to-feed ratio (GTF).

Hormone treatments. Synthetic 3,3',5-triiodo-L-thyronine (Product T2877, purity 95-98%, Lot No. 28F-0086) was obtained from Sigma Chemical Co. (St. Louis, MO). Synthetic human pancreatic growth releasing factor (hpGRF$_{1-44}$) was obtained from Pitman-Moore, Inc. (Terre Haute, IN). Four treatments were randomly assigned to 16 pens of birds (4 birds/pen): control feed plus buffer injection (CF+BI), CF+GRF, $T_3$+BI, and $T_3$+GRF. Beginning at 35 days of age, broiler cockerels were given three daily intramuscular injections of buffer (0.05M sodium acetate, pH 5.0) or GRF dissolved in buffer (10 µg/kg body weight) each day at 0800, 1600, and 2400 hr. Each bird was weighed a 3 day intervals to adjust GRF dosage.

Dietary treatments consisted of either CF or feed containing 0.25 ppm $T_3$ ($T_3$). At 49 days of age, chickens were starved for 24 hours and killed for determination of final body, abdominal fat pad, and liver weights. Carcasses from one-half of the birds in each pen (2 birds/pen) were frozen for determination of body composition by proximate analysis. Each frozen carcass, including the liver and abdominal fat, was ground twice in meat grinder fitted with a one-quarter inch dye (Biro Model 5, Biro Mfg. Co., Marblehead, OH). Aliquots of the ground meat were dried at 80° C. for moisture determination. Dried samples were analyzed for protein by macro-Kjeldahl, fat by ether extraction, and ash contents according to established analytical procedures. Body composition data are presented as a percent of final body weight at 7 weeks of age.

Statistical analyses. All data were analyzed with the pen as the experimental unit since dietary treatments were applied to the pen and feed consumption was determined for each pen. Least squares regression analysis was used to test for effects of treatments on ADG, ADFC, GTF, body weight and body composition. Significant differences (P<0.05) among treatments were determined by Fisher's least significant difference test.

TABLE 1

Composition of high-protein broiler grower/finisher ration

| Ingredients | % |
|---|---|
| Corn | 50.410 |
| Soybean 48 | 31.782 |
| Corn gluten meal | 5.000 |
| Poultry by-product | 3.500 |
| Vegetable oil | 5.246 |
| Limestone | 1.011 |
| Dicalcium phosphate | 1.499 |
| L-Lysine 98 | 0.067 |
| DL-Methionine | 0.086 |
| NaCl | 0.399 |
| Trace mineral premix | 0.500 |
| Vitamin premix | 0.500 |
| Grand total | 100% |
| Analysis |  |
| Protein | 25.0% |
| Fat | 7.8% |
| Fiber | 2.7% |
| Metabolizable energy | 3250 kcal/kg feed |

RESULTS

Growth Performance and Body Composition

There was no effect of dietary $T_3$ or daily intramuscular injections of GRF on ADG, ADFC or GTF of broiler chickens (Table 2). Neither dietary $T_3$ nor daily GRF injections alone or in combination had a significant effect on final body weight (i.e., 7 weeks of age) or the relative liver weight of broiler chickens (Table 3). Dietary $T_3$ alone reduced (P<0.05) abdominal fat weight by 31% when compared to the CF+BC group, whereas the combination of $T_3$+GRF reduced (P<0.05) abdominal fat by 25% (Table 3). The average abdominal fat weight of the CF+GRF group (1.48% BW) was not significantly different from that of the CF+BC group (1.62% BW).

The combination of dietary $T_3$ and daily GRF injections reduced (P<0.05) total body fat content of 7-week-old chickens by 20% when compared to either the CF+BI or CF+GRF groups (Table 4). The reduction of body fat content in birds treated with $T_3$+GRF was accompanied by a slight increase in body water and body protein contents. Dietary $T_3$ alone reduced body fat content by 10% although this difference was not statistically significant from the CF+BI group.

TABLE 2

Growth and Feed Efficiency of Broiler Cockerels Given Three Daily Intramuscular Injections of GRF and Fed T, from 5 to 7 Weeks of Age

| Treatment | ADG | ADFC | GTF |
|---|---|---|---|
| CF + BI | 84.1 ± 2.1 | 185.3 ± 1.6 | 0.453 ± 0.01 |
| $T_3$ + BI | 76.5 ± 3.0 | 185.1 ± 7.1 | 0.414 ± 0.01 |
| CF + GRF | 84.9 ± 5.4 | 188.6 ± 3.9 | 0.449 ± 0.02 |
| $T_3$ + GRF | 75.8 ± 3.8 | 180.4 ± 2.6 | 0.420 ± 0.02 |

Each valve represents the mean ± SEM of four pens (4 birds/pen).

TABLE 3

Final Body Weight (BW) and Relative Weights (% BW) of Liver and Abdominal Fat Pad in Broiler Cockerels Given Three Daily Intramuscular Injections of GRF and Fed $T_3$ from 5 to 7 Weeks of Age

| Treatment | BW (kg) | % BW Liver | % BW Abdominal fat |
|---|---|---|---|
| CF + BI | 2.84 ± 0.01 | 2.20 ± 0.11 | 1.62 ± 0.58$^a$ |
| $T_3$ + BI | 2.75 ± 0.05 | 1.99 ± 0.09 | 1.12 ± 0.11$^c$ |
| CF + GRF | 2.88 ± 0.06 | 2.09 ± 0.06 | 1.48 ± 0.17$^{ab}$ |
| $T_3$ + GRF | 2.76 ± 0.07 | 2.25 ± 0.12 | 1.21 ± 0.07$^{bc}$ |

Means within a column possessing a different superscript are significantly (P <0.05) different. Each value represents the mean ± SEM of four pens of birds (4 birds/pen).

TABLE 4

Body composition of broiler cockerels given three daily intramuscular injections of GRF and fed $T_3$ from 5 to 7 weeks of age

| Treatment | Water | Protein* | Fat | Ash |
|---|---|---|---|---|
| CF + BI | 66.5 ± 0.37$^c$ | 17.4 ± 0.14$^{ab}$ | 11.2 ± 0.31$^a$ | 2.26 ± 0.03 |
| $T_3$ + BI | 67.6 ± 0.70$^{ab}$ | 17.1 ± 0.26$^b$ | 10.0 ± 0.78$^{ab}$ | 2.24 ± 0.08 |
| CF + GRF | 67.0 ± 0.50$^{bc}$ | 17.2 ± 0.16$^{ab}$ | 11.4 ± 0.63$^a$ | 2.27 ± 0.05 |
| $T_3$ + GRF | 68.4 ± 0.30$^a$ | 17.6 ± 0.09$^a$ | 9.0 ± 0.27$^b$ | 2.31 ± 0.09 |

Each value represents the mean ± of four pens (2 birds/pen) at 7 weeks of age. Means within a column possessing a different superscript are significantly (P <0.05) different. (*Significant differences among protein means are at P <0.09).

EXAMPLE 2

Effect of Three Daily Intravenous Injections of Growth Hormone Releasing Factor and Dietary Triiodothyronine on Growth, Feed Efficiency, and Body Composition of Broiler Chickens The purpose of this Example was to determine if multiple daily intravenous injections of GRF and dietary $T_3$ could be used to increase lean body mass of broiler chickens.

MATERIALS AND METHODS

Bird management. Day-old broiler cockerels (Ross X Arbor Acre strain) were obtained from a commercial hatchery (Longnecker Hatchery, Elizabethtown, PA) and randomly assigned in groups of four birds to pens in a heated-battery brooder. Chicks were provided with a commercial broiler-starter ration (Pennfield Corp., Lancaster, PA), containing 3100 kcal metabolizable energy/kg feed and 23% crude protein, and water ad libitum. At 3 weeks of age, birds were transferred to wire pens held in a controlled-environment room. From 3 to 7 weeks of age, birds were maintained under a 20L:4D light-dark cycle at 21° C. and continuously provided with water and a commercial broiler-finisher ration containing 3250 kcal metabolizable energy/kg feed and 20% crude protein. Broiler cockerels were given three daily intravenous injections of either buffer (0.1M phosphate buffer, pH 7.0; BC) or GRF dissloved in buffer (25 μg/kg body weight) at 0800, 1600, and 2400 hr. Dietary treatments consisted of either control feed (CF) containing dextrose premix or 0.25 ppm $T_3$ ($T_3$) from 5 to 7 weeks of age.

Dietary $T_3$ and GRF Treatments. Four treatments were randomly assigned to pens in a randomized-complete-block design with three replicate pens per treatment. The four treatments were initiated at 5 weeks of age and consisted of CF plus buffer injection (0.1M phosphate, pH 7) (CF+BI), 0.25 ppm $T_3$ plus BI ($T_3$+BI), CF plus GRF injection (25 μg/kg three times a day) (CF+GRF), and $T_3$+GRF. All birds were weighted at three day intervals to adjust the daily GRF dosage. Recombinant-derived human growth hormone-releasing factor (rhGRF$_{1-44}$) was obtained from Pitman-Moore, Inc. (Terre Haute, IN).

The average daily gain (ADG), average daily feed consuption (ADFC) and the gain-to-feed ratio (GTF) were determined for the two week period (5 to 7 weeks of age). At the end of the experiment (7 weeks of age), each bird was killed to obtain the final body, abdominal fat and liver weights. Carcasses were frozen for determination of body composition as described in Example 1.

Statistical analyses. A randomized-complete-block design was used in which the four treatments were replicated in three pens. The growth data were analyzed with the pen as the experimental unit, since feed comsumption was determined for each pen of four birds. Significant differences ($P \leq 0.05$) due to the main effect of treatment were determined by Fisher's Least Significant Difference test.

RESULTS

Growth Performance and Body Composition

Treatment of broiler chickens with dietary $T_3$ or daily intravenous injections of GRF alone, or in combination, did not significantly affect ADG, ADFC or the GTF ratio (Table 5). Similarly, there were no treatment effects on final body weight or relative liver weight (Table 6). However, the $T_3$+GRF combination reduced ($P<0.05$) abdominal fat weight by 28% when compared to the CF+BI group. Although not significantly different from the control group, dietary $T_3$ alone reduced the abdominal fat weight by 20%. Dietary $T_3$ treatment alone reduced body fat content by 10% and increased body water content by 2%. However, the combination of dietary $T_3$ and three daily intravenous injections of GRF reduced ($P<0.05$) body fat content by 21% and increased body water content by 3% without affecting body protein and ash contents (Table 7). The GRF treatment alone did not have any effect on growth rate, feed efficiency or body composition. These data clearly show a synergism between GRF and $T_3$ treatments in reduction of body fat content of broiler chickens. Since the $T_3$+GRF treatment did not alter final body weight, the 21% reduction in body fat content was more favorably replaced by an increase in body water content.

TABLE 5

Growth Performance of Broiler Cockerels Given Three Daily Intravenous Injections of GRF and Fed $T_3$ from 5 to 7 Weeks of Age

| Treatment | ADG | ADFC | GTF |
| --- | --- | --- | --- |
| CF + BI | 72.4 ± 3.2 | 159.2 ± 6.8 | 0.454 ± 0.001 |

TABLE 5-continued

Growth Performance of Broiler Cockerels Given Three Daily Intravenous Injections of GRF and Fed $T_3$ from 5 to 7 Weeks of Age

| Treatment | ADG | ADFC | GTF |
| --- | --- | --- | --- |
| $T_3$ + BI | 70.7 ± 5.3 | 157.0 ± 7.2 | 0.448 ± 0.021 |
| CF + GRF | 67.3 ± 1.9 | 155.1 ± 1.1 | 0.434 ± 0.010 |
| $T_3$ + GRF | 69.3 ± 1.2 | 156.3 ± 0.3 | 0.441 ± 0.007 |

Each valve represents the mean ± SEM of three pens (4 birds/pen) for the two week experimental period (5 to 7 weeks of age).

TABLE 6

Final Body Weight (BW), Relative Weights of Liver and Abdominal Fat in Broiler Cockerels Given Three Daily Intravenous Injectsions of GRF and Fed $T_3$ from 5 to 7 Weeks of Age

| Treatment | BW (kg) | % BW Liver | % BW Abdominal Fat |
| --- | --- | --- | --- |
| CF + BI | 2.82 ± 0.06 | 2.14 ± 0.07 | 1.92 ± 0.15$^a$ |
| $T_3$ + BI | 2.82 ± 0.06 | 2.06 ± 0.05 | 1.54 ± 0.14$^{ab}$ |
| CF + GRF | 2.79 ± 0.08 | 2.07 ± 0.05 | 1.74 ± 0.17$^a$ |
| $T_3$ + GRF | 2.83 ± 0.07 | 2.10 ± 0.10 | 1.39 ± 0.13$^b$ |

Each value represents the mean ± SEM of twelve cockerels at 7 weeks of age. Means within a column possessing a different superscript are significantly ($P<0.05$) different.

TABLE 7

Body composition of broiler cockerels given three daily intravenous injections of GRF and fed $T_3$ from 5 to 7 weeks of age

| Treatment | Water | Protein | Fat | Ash |
| --- | --- | --- | --- | --- |
| CF + BI | 65.5 ± 0.45$^c$ | 18.7 ± 0.16 | 12.8 ± 0.56$^a$ | 2.44 ± 0.03 |
| $T_3$ + BI | 67.0 ± 0.50$^{ab}$ | 18.8 ± 0.19 | 11.5 ± 0.64$^{ab}$ | 2.45 ± 0.04 |
| CF + GRF | 66.2 ± 0.36$^{bc}$ | 18.9 ± 0.15 | 12.1 ± 0.50$^a$ | 2.44 ± 0.04 |
| $T_3$ + GRF | 67.3 ± 0.28$^a$ | 19.0 ± 0.12 | 10.1 ± 0.36$^b$ | 2.43 ± 0.04 |

Each value represents the mean ± of twelve cockerels at 7 weeks of age. Means within a column possessing a different superscript are significantly ($P<0.05$) different.

CONCLUSIONS

These Examples clearly show that stimulation of endogenous GH secretion in $T_3$-fed chickens can be achieved by either intramuscular or intravenous injection of GRF. Although the intravenous route of administering GRF appears to be more effective than intramuscular injections in reducing the body fat content of $T_3$-fed broiler chickens, the high protein ration used in Example 1 reduced the abdominal fat weight of the control group (CF+BI) by 16% when compared to the control group in Example 2. However, the use of a high protein feed (i.e., 25% crude protein) to reduce body fat is not always economically possible. The combination of GRF treatment with dietary $T_3$ during the last portion of the growth period of broiler chickens provides a method for dramatically reducing body fat content of poultry meat.

What is claimed is:

1. A method for lowering the extent of fat deposition in living poultry grown substantially for meat production, during the normal growth cycle of the poultry, without detracting substantially from the growth rate, which comprises:
   (a) providing exogenous metabolically-active thyroid hormone to the living poultry during the finishing phase of the normal growth cycle of the poultry, said providing of the exogenous metabolically-active thyroid hormone being delayed until the poultry are at least about 3 weeks of age, the exogenous metabolically-active thyroid hormone having at least about 50% of the receptor-binding capacity of 3,3',5-triiodo-L-thyronine, and the dosage of exogenous metabolically-active thyroid hormone being sufficient to provide a level of plasma thyroid hormone level which has at least about 150% of the bioactivity of the normal endogenous level of 3,3',5-triodo-L-thyronine, and (b) increasing endogenous growth hormone levels, at least during the finishing phase of the normal growth cycle of the poultry, by administering natural or synthetic exogenous growth hormone releasing factor or natural or synthetic thyrotropin releasing hormone or an analog thereof, or a combination thereof, to said living poultry.

2. A method according to claim 1 wherein the metabolically-active thyroid hormone is exogenous 3,3',5-triiodo-L-thyronine, and the said hormone is orally administered to the poultry.

3. A method according to claim 2, wherein the said hormone is fed to poultry in the finishing feed formula, in the amount of at least about 0.1 to 1 part per million based on the weight of a daily ration of feed.

4. A method according to claim 3, wherein said plasma thyroid hormone level is about 150% to about 250% of said normal endogenous level.

5. A method according to claim 1, wherein the poultry are treated in accordance with the said method for about two to five weeks.

6. A method according to claim 5 wherein the poultry are broiler chickens having normal or enhanced pituitary function, wherein the body fat content of the broiler chicken is decreased as a result of said method by at least about 15% by weight, compared to untreated broiler chickens.

7. A method according to claim 1, wherein the exogenous growth hormone releasing factor is provided only during the said finishing phase.

8. A method according to claim 1, wherein said growth hormone releasing factor is a synthetic polypeptide having 29 amino acid residues.

9. A method for lowering the extent of fat deposition in living poultry, grown substantially for meat production, having normal or enhanced pituitary function, during the normal growth cycle of the poultry, without detracting from the normal growth rate, which consists essentially of:

(a) waiting until the poultry are more than two weeks of age and then feeding to the poultry a finishing feed formula containing at least about 0.01 but less than 3 parts per million, based on the weight of the feed, of a metabolically-active thyroid hormone of the formula

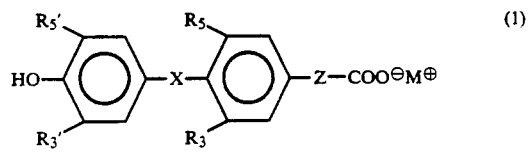

wherein X is O, S, or $CH_2$,

Z is $C_2$-$C_4$ alkylene or amino-substituted $C_2$-$C_4$ alkylene, $M^+$ is a physiologically acceptable cation, $R_3$ and $R_5$ are H or iodo, at least one of them being iodo, $R_3'$ and $R_5'$ are iodo, or hydrogen or —A—COO—$M^+$, where A is $C_2$-$C_4$ alkylene and $M^+$ is a physiologically acceptable cation, provided, that when $R_3'$, $R_5'$, $R_3$ and $R_5$ are all iodo, then Z—COO$^-$ is the residue of the anion of acetic or propionic acid; said thyroid hormone having at least about 50% of the receptor-binding capacity of 3,3', 5-triiodo-L-thyronine, and administering a composition selected from the group consisting of exogenous natural growth hormone releasing factor or a biologically active analog thereof, exogenous synthetic growth hormone releasing factor or a biologically active analog thereof, natural thyrotropin releasing hormone or a biologically active analog thereof, synthetic thyrotropin releasing hormone or a biologically active analog thereof, and mixtures thereof, to said poultry, after said poultry are more than two weeks of age.

10. A method according to claim 9, wherein the feed formula contains about 0.01 to 1 part per million of said thyroid hormone, on the same basis.

11. A method according to claim 10, wherein the said thyroid hormone is 3,3',5-triiodo-L-thyronine, and the feed formula contains about 0.1 to 0.5 part per million of said hormone, on the same basis.

* * * * *